United States Patent [19]

Imamura et al.

[11] Patent Number: 4,670,430

[45] Date of Patent: Jun. 2, 1987

[54] FINELY POWDERED POLYVALENT METAL SALTS OF 2-MERCAPTOPYRIDINE-N-OXIDE, METHOD FOR PRODUCING THE SAME, AND ANTIBACTERIAL COMPOSITIONS COMPRISING THE SAME

[75] Inventors: Takashi Imamura; Toshio Nozaki; Kenji Nishino, all of Wakayama; Hiroyuki Kanai, Tochigi, all of Japan

[73] Assignee: Kao Corporation, Tokyo, Japan

[21] Appl. No.: 627,479

[22] Filed: Jul. 3, 1984

[30] Foreign Application Priority Data

Jul. 6, 1983 [JP] Japan ................... 58-122845
Apr. 24, 1984 [JP] Japan ................... 59-82690

[51] Int. Cl.$^4$ ................... C07D 213/89; A61K 7/06; A61K 7/08; A61K 31/555
[52] U.S. Cl. ................... 514/188; 546/6; 424/70; 424/DIG. 14
[58] Field of Search ................... 546/6; 514/188

[56] References Cited

U.S. PATENT DOCUMENTS

| | | | |
|---|---|---|---|
| 3,723,325 | 3/1973 | Parran, Jr. ................... | 424/78 |
| 4,323,683 | 4/1982 | Bolich, Jr. et al. ................... | 546/243 |
| 4,345,080 | 8/1982 | Bolich, Jr. ................... | 546/6 |
| 4,421,749 | 12/1983 | Pauling ................... | 546/6 |

FOREIGN PATENT DOCUMENTS 70046 1/1983 European Pat. Off. .

OTHER PUBLICATIONS

DiFazio, Chem Abs 75, 91307t (1970).
Davis et al., Chem Abs 100, 39616 (11-9-83).

Primary Examiner—Mark L. Berch
Attorney, Agent, or Firm—Oblon, Fisher, Spivak, McClelland & Maier

[57] ABSTRACT

Polyvalent metal salts of 2-mercaptopyridine-N-oxide which are made into fine powder in which particles having a size below 0.2 micron are contained in amounts not smaller than 50 wt %.

Preparing process of the above and antibacterial compositions comprising the above are also disclosed.

When the finely powdered polyvalent metal salts of 2-mercaptopyridine-N-oxide are incorporated into shampoo or rinse compositions, dispersion stability of the salts is remarkably improved with the enhanced adsorbability of the particles on the skin and hair, thus antibacterial and dandruff-removing actions owing to the salts are further improved.

6 Claims, No Drawings

FINELY POWDERED POLYVALENT METAL SALTS OF 2-MERCAPTOPYRIDINE-N-OXIDE, METHOD FOR PRODUCING THE SAME, AND ANTIBACTERIAL COMPOSITIONS COMPRISING THE SAME

BACKGROUND OF THE INVENTION (i) Field of the Invention:

This invention relates to finely powdered polyvalent metal salts of 2-mercaptopyridine-N-oxide and to a method for producing same. It also relates to antibacterial compositions comprising such metal salts.

(ii) Description of the Prior Art:

Polyvalent metal salts of 2-mercaptopyridine-N-oxide (which may be hereinafter referred to simply as polyvalent metal salts) are known to be effective as antibacterial agents and are widely used not only as ordinary bactericides, but also as dandruff removers being added to shampoo, rinse and the like. The polyvalent metals of the salts are, for example, calcium, magnesium, barium, strontium, zinc, cadmium, tin, zirconium and the like, of which zinc is widely used.

However, these polyvalent metal salts, e.g. zinc salt has a solubility in water of 15 ppm at 25° C. and is thus sparingly soluble in water with a high specific gravity, so that they are sold and supplied in the form of a powder or an aqueous dispersion. Because of the high specific gravity, the metal salts have the disadvantage that even when suspended or dispersed in solvent, they are liable to coagulate, settle and separate.

Several shampoos and rinses containing the polyvalent metal salts are put on the market. In order to stably incorporate the salts into shampoo or rinse compositions, it is unavoidable to make them highly viscous or to add specific types of polymers or clay minerals. This leads to the disadvantage that the compositions become poor in performance, e.g. with shampoos, the foaming ability becomes poor with objectionable feeling to the touch after washing of the hair.

Recently, several methods of stably keeping such metal salts in compositions have been proposed including a method using the salts in combination with hydroxyalkyl celluloses (Japanese laid-open Application No. 57-80499), a method using the salts in combination with amphoteric polymer compounds (Japanese Laid-open Application No. 54-41909), a method in which HPC is used in combination (Japanese Laid-open Application No. 35-97010), and a method in which polyacrylic acid/polyacrylates are used in combination.

However, all these methods still make use of the specific types of polymers and thus problems on the rise of cost and the performance of the products are not solved. Moreover, these methods are all techniques of applications to shampoos. The possibility of applications to other types of products are not made clear.

SUMMARY OF THE INVENTION

In view of the above, we made intensive studies in order to stably add the polyvalent metal salts serving as excellent antibacterial agents to ordinary shampoos, hair rinses and the like. As a result, it was found that when the salts are finely divided so that the particles thereof are below a specific size, dispersion stability of the salts is remarkably improved with the adsorbability of the fine particles on the skin and hair being also improved. Accordingly, shampoos, hair rinses and the like cosmetics which comprise the polyvalent metal salts have improved antibacterial and dandruff-removing actions.

We also found that it was difficult or took a long time to obtain finely divided polyvalent metal salts through ordinary media with a size of 0.6 mm to 3 mm as used in sand mills, sand grinders or the like. However, fine particles could be obtained efficiently within a short time by agitating a dispersion of the salts along with media having a size ranging from 0.5 mm to 0.1 mm.

It was also found that agitation of a dispersion of the salts comprising a specific type of dispersant resulted in more finely divided particles.

According to the present invention, there are provided finely divided polyvalent metal salts of 2-mercaptopyridine-N-oxide in which not less than 50 wt % of the finely divided salt has a particle size below 0.2 micron. The size is preferably below 0.1 micron. Also, a method is provided for producing the finely divided polyvalent metal salts and antibacterial compositions comprising such salts.

DETAILED DESCRIPTION OF THE INVENTION AND PREFERRED EMBODIMENTS

The finely divided polyvalent metal salts according to the invention should have a size distribution in which not less than 50 wt % of the particles have a size below 0.2 micron. Preferably, the finely divided metal salts have such a size distribution of particles comprising not less than 50 wt % of the particles having a size below 0.2 micron, not greater than 15 wt % of the particles having a size ranging from 0.5 to 1.0 micron, and not greater than 2 wt % of the particles exceeding 1.0 micron, with an average size below 0.2 micron. More preferably, the particles have a size distribution comprising not less than 70 wt % of the particles having a size below 0.2 micron, not greater than 10 wt % of the particles having a size ranging from 0.5 to 1 micron and substantially free of particles exceeding 1.0 micron, with an average size below 0.15 micron.

Most preferably, the finely divided polyvalent metal salt has a size distribution in which not less than 50 wt % of particles have a size below 0.1 micron. In this case, a preferable size distribution is such that not less than 50 wt % of the particles have a size below 0.1 micron, not greater than 15 wt % of the particles have a size ranging from 0.2 to 0.5 micron and not greater than 5 wt % of the particles having a size exceeding 0.5 micron, with an average size below 0.1 micron. Most preferably, the size distribution is such that not less than 70 wt % of the particles have a size below 0.1 micron, not greater than 10 wt % of the particles have a size ranging from 0.2 to 0.5 micron, and particles having a size exceeding 0.5 micron are not substantially contained, with an average size below 0.08 micron.

The finely divided polyvalent metal salts of the invention may be prepared by agitating a dispersion of the salt, as it is or admixed with a salt of (meth)acrylic acid-styrenesulfonic acid copolymer having an average molecular weight of from 10,000 to 1,000,000, along with rigid media having a size below 0.5 mm, thereby finely dividing the salt by the shearing strength of the media into fine particles.

Starting polyvalent metal salts are favorably used in the form of an aqueous dispersion. Commercially sold dispersions, dispersions obtained by dispersing commercially sold powders of such salts, or suitably prepared dispersions may be used. The content of the salt in the dispersion is preferably in the range of from 5 to 70 wt %. In view of the production efficiency, higher concentrations are more preferable. It will be noted that commercially sold dispersants of the salts usually contain 50 wt % of the effective component.

The salts of (meth)acrylic acidstyrenesulfonic acid copolymer used as the dispersant are water-soluble salts of copolymer of acrylic acid and/or methacrylic acid and styrenesulfonic acid, and may be prepared by a known method. The molar ratio of (meth)acrylic acid and styrenesulfonic acid in the copolymer ranges from 1/10 to 10/1, preferably from $\frac{1}{3}$ to 7/1. The molecular weight is from 10,000 to 1,000,000, preferably from 100,000 to 700,000. The molecular weight is important in the practice of the invention. If the molecular weight is smaller than 10,000, the polyvalent metal salts may not be finely divided, or once formed particles may be considerably coagulated. On the other hand, when the molecular weight is larger than 1,000,000, it becomes difficult to handle because the high viscosity of the water-soluble copolymer salt itself.

The salts of the copolymers include salts of sodium, potassium, ammonium, monoethanolamine, diethanolamine, triethanolamine, monoisopropanolamine, diisopropanolamine, triisopropanolamine, 2-amino-2-methylpropane-1,3-diol and the like. Non-neutralized carboxyl groups may be left to an extent of impeding the performance of the copolymer salts.

Moreover, the copolymers may comprise a third component in amounts not impeding the nature thereof. Examples of the third component include styrene, acrylamide, sulfonic acids such as methacrylsulfonic acid, vinylsulfonic acid and the like, 2-hydroxyethyl acrylate, various acrylates, various methacrylates, N-methylolacrylamide, and other copolymerizable monomers.

The water-soluble copolymer salts are generally added in an amount not smaller than 0.1 wt %, preferably from 0.5 to 10 wt %.

The media have a size below 0.5 mm, preferably from 0.1 to 0.2 mm. Although fine division of the polyvalent metal salts is possible using media having a size smaller than 0.1 mm, the mixture of the media and the polyvalent metal salts is so high in viscosity that handling becomes difficult. The materials for the media are rigid materials such as, for example, Ottawa sand, glass, alumina, zircon and the like, of which glasses are preferred.

The apparatus in which the polyvalent metal salts and the media are agitated for fine division of the salts may be sand mills, sand grinders and the like. Any known types of sand mills and sand grinders including vertical and horizontal types may be used in the practice of the invention. Discs may be of any ordinarily used types.

The temperature at which fine division is effected is preferably from 5° to 30° C. At temperatures exceeding 30° C., it takes a long time before completion of the fine division, making the fine division difficult.

The mixing ratio of the media and the dispersion of the metal salt is from 40/60 to 80/20, preferably from 60/40 to 70/30, on the volume basis.

After finely divided, the polyvalent metal salt is filtered under pressure or centrifugally separated to separate the media and the salt dispersion from each other. If necessary, the media may be washed with water thereby obtaining a finely divided metal salt.

The thus obtained finely divided metal salt comprises 50 wt % or more of particles having a size below 0.2 micron, preferably 0.1 micron (the size and its distribution are determined using a centrifugal automatic size distribution measuring instrument CAPA-500 (available from Horiba Seisakusho Co., Ltd.)). Because such fine particles have good dispersability, the dispersion obtained is stable over a long term. The finely divided metal salts are more stable and more adsorbable on the hair, skin, bark, building materials and the like and are better in antibacterial effect than known counterparts. Accordingly, such finely divided salts can be utilized not only as dandruff in hair cosmetics, but also as ordinary aqueous bactericides using the salts as a dispersion which has never been used because of the problem of dispersion stability.

The present invention is described by way of examples.

EXAMPLE 1

70 ml of a commercially available dispersion of zinc salt of 2-mercaptopyridine-N-oxide and 130 ml of glass beads (media) having a size of 0.1 to 0.2 mm or 0.6 to 0.8 mm were mixed (media/dispersion ratio by volume =65/35) and placed in a 400 ml sand grinder (made by Igarashi Machine Manufacturing Co., Ltd.). Grinder discs were rotated for 3 hours at a peripheral speed of 6 m/second. The temperature within the grinder was 20° to 25° C. The resulting dispersion was filtered under pressure to obtain 35 ml of finely divided zinc salt. The media was washed twice each with 70 ml of water. As a result, 98 wt % of the zinc salt was recovered.

The finely divided zinc salt had, as shown in Table 1 below, a size distribution in which particles having a size below 0.2 micron were contained in an amount of 83 wt %.

TABLE 1

| Zinc Salt Dispersion | | Size of Media | | | | | |
|---|---|---|---|---|---|---|---|
| | | 0.6–0.8 mm | | | 0.1–0.2 mm | | |
| | | Treating Time | | | | | |
| | | 1 hour | 3 | 8 | 1 hour | 3 | 8 |
| Size Distribution (wt %) | over 1.0 (μ) | 0% | 0 | 0 | 0 | 0 | 0 |
| | 1.0–0.8 | 13 | 12 | 10 | 1 | 0 | 0 |
| | 0.8–0.6 | 10 | 7 | 3 | 3 | 0 | 0 |
| | 0.6–0.4 | 23 | 14 | 9 | 9 | 0 | 0 |
| | 0.4–0.2 | 38 | 40 | 29 | 32 | 17 | 14 |
| | below 0.2 | 16 | 27 | 49 | 55 | 83 | 86 |
| Average Size (μ) | | 0.38 | 0.31 | 0.21 | 0.19 | 0.12 | 0.11 |

EXAMPLE 2

70 ml of a commercially available dispersion of zinc salt of 2-mercaptopyridine-N-oxide and 130 ml of glass beads (media) having a size of 0.5 mm were mixed (media/dispersion ratio by volume=65/35) and placed in a 400 ml sand grinder (made by Igarashi Machine Manufacturing Co., Ltd.). Grinder discs were rotated for 8 hours at a peripheral speed of 6 m/second. The temperature within the grinder was 20° to 25° C. The resulting dispersion was filtered under pressure to obtain 32 ml of finely divided zinc salt.

The finely divided zinc salt had, as shown in Table 2, a size distribution in which particles having a size below 0.2 micron were contained in an amount of 54 wt %.

EXAMPLE 3

70 ml of a commercially available dispersion of zinc salt of 2-mercaptopyridine-N-oxide and 130 ml of glass beads (media) having a size of 44 to 63 microns were mixed (media/dispersion ratio by volume=65/35) and placed in a 400 ml sand grinder (made by Igarashi Machine Manufacturing Co., Ltd.). Grinder discs were rotated for 3 hours at a peripheral speed of 5 m/second. The temperature within the grinder was 20° to 25° C. The resulting dispersion was filtered under pressure to obtain 31 ml of finely divided zinc salt.

The finely divided zinc salt had, as shown in Table 2, a size distribution in which particles having a size below 0.2 micron were contained in an amount of 88 wt %.

EXAMPLE 4

80 ml of a commercially available dispersion of zinc salt of 2-mercaptopyridine-N-oxide and 120 ml of glass beads (media) having a size of 0.1 to 0.2 mm were mixed (media/dispersion ratio by volume=60/40) and placed in a 400 ml sand grinder (made by Igarashi Machine Manufacturing Co., Ltd.). Grinder discs were rotated for 4 hours at a peripheral speed of 6 m/second. The temperature within the grinder was 20° to 25° C. The resulting dispersion was filtered under pressure to obtain 37 ml of finely divided zinc salt.

The finely divided zinc salt had, as shown in Table 2, a size distribution in which particles having a size below 0.2 micron were contained in an amount of 64 wt %.

25 TEXH, by Serizawa Iron Works Co., Ltd.), grinder discs were rotated for 6 hours at a peripheral speed of 12 m/second. The mixture of the glass beads and the zinc salt dispersion was circulated to the mixing vessel at a rate of 8 liters/hour. The amounts of the mixture residing in the sand grinder and the mixing vessel were made equal.

The temperature in the sand grinder was maintained at 20° to 25° C. because the mixture was cooled in the mixing vessel.

Thereafter, the mixture of the glass beads and the finely divided zinc salt was withdrawn and subjected to a centrifugal separator in which the glass beads and the finely divided salt were separated from each other. The separated glass beads were transferred to the mixing vessel for reuse.

As a result, 23.8 kg of the finely divided zinc salt was obtained. When the glass beads were washed with 28 kg of water, the starting zinc salt could be substantially recovered.

The finely divided zinc salt had, as shown in Table 2, a size distribution in which 88 wt % of the particles had a size below 0.2 micron.

TABLE 2

| Zinc Salt Despersion | | Example 2 | Example 3 | Example 4 | Example 5 | Example 6 | Example 7 |
| --- | --- | --- | --- | --- | --- | --- | --- |
| Size | over 1.0 (μ) | 0 | 0 | 0 | 0 | 0 | 0 |
| Distribution | 1.0–0.8 | 2 | 0 | 2 | 0 | 0 | 0 |
| (wt %) | 0.8–0.6 | 2 | 0 | 2 | 0 | 0 | 0 |
| | 0.6–0.4 | 8 | 5 | 7 | 2 | 2 | 5 |
| | 0.4–0.2 | 34 | 7 | 25 | 13 | 15 | 7 |
| | below 0.2 | 54 | 88 | 64 | 85 | 83 | 88 |
| Average Size (μ) | | 0.19 | 0.13 | 0.16 | 0.11 | 0.12 | 0.13 |

EXAMPLE 5

60 ml of a commercially available dispersion of zinc salt of 2-mercaptopyridine-N-oxide and 149 ml of glass beads (media) having a size of 0.1 to 0.2 mm were mixed (media/dispersion ratio by volume=70/30) and placed in a 400 ml sand grinder (made by Igarashi Machine Manufacturing Co., Ltd.). Grinder discs were rotated for 4 hours at a peripheral speed of 6 m/second. The temperature within the grinder was 20° to 25° C. The resulting dispersion was filtered under pressure to obtain 29 ml of finely divided zinc salt.

The finely divided zinc salt had, as shown in Table 2, a size distribution in which particles having a size below 0.2 micron were contained in an amount of 85 wt %.

EXAMPLE 6

504 ml of a commercially available dispersion of zinc salt of 2-mercaptopyridine-N-oxide and 896 ml of glass beads (media) having a size of 0.1 to 0.2 mm were mixed (media/dispersion ratio by volume=64/36) and placed in a 1400 ml horizontal sand grinder (Dyno Mill: Willy A. Bachofen, Engineering Works). Grinder discs were rotated for 2.5 hours at a peripheral speed of 10 m/second. The temperature within the grinder was 20° to 25° C.

The finely divided zinc salt had, as shown in Table 2, a size distribution in which particles having a size below 0.2 micron were contained in an amount of 83 wt %.

EXAMPLE 7

28 kg of a commercially available dispersion of zinc salt of 2-mercaptopyridine-N-oxide and 58 kg of glass beads having a size of 0.1 to 0.2 mm were mixed in a mixing vessel. In a horizontal sand grinder (Pearl Mill

EXAMPLE 8

$^{35}$S-labelled zinc salt of 2-mercaptopyridine-N-oxide of the invention was dispersed in 500 ml of an aqueous solution of 1.0% sodium polyoxyethylene(2) lauryl sulfate. In the dispersion was placed 30 mg of a bundle of the hair, followed by immersing for 1 minute while agitating at 100 r.p.m. Thereafter, the hair bundle was rinsed twice with running water for 15 seconds and air-dried, after which 10 mg of the hair was exactly weighed and placed in a 20 ml vial. In the vial, it was dissolved in 1 ml of Soluen 350, to which was added 100 ml of a scintillator, followed by counting by a liquid scintillation counter to measure an amount of an adsorbed zinc salt. The results are shown in Table 3.

TABLE 3

| Concentration of Zinc Salt Dispersion (%) | 0.5 | 1.0 | 1.5 | 2.0 |
| --- | --- | --- | --- | --- |
| Product of Invention* | 0.19 | 0.25 | 0.53 | 0.98 |

| *Product of Invention | |
| --- | --- |
| Average size | 0.11μ |
| <0.2μ | 78.0% |
| 0.5–1.0μ | 8.7% |
| over 1.0μ | 0% |
| μg/10 mg of hair | |

EXAMPLE 9

A commercially available zinc salt and a zinc salt obtained according to the invention were each dispersed in water in order to compare the resulting dispersions with respect to dispersion stability. The results are showin in Table 4.

TABLE 4

| | Product of Invention (Example 3) |
|---|---|
| Average size | 0.13μ |
| Dispersion stability | stable |

Dispersion stability test: each zinc salt was dispersed in water in a concentration of 1%, which was placed in a test tube and allowed to stand for 10 days. After 10 days, the state of the dispersion was visually judged.

EXAMPLE 10

23 g of a powder of zinc salt of 2-mercaptopyridine-N-oxide, 4.5 g of a water-soluble copolymer salt of the formula having a molecular weight of 680,000;

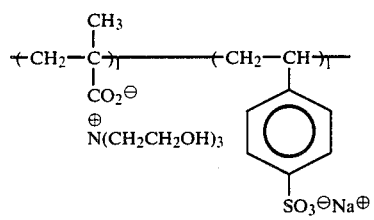

63 g of water, and 187 g of glass beads (media) having a size of 0.1 to 0.2 mm were mixed (media/dispersion ratio by volume=63/37) and placed in a 400 ml sand grinder (made by Igarashi Machine Manufacturing Co., Ltd.). In the grinder, discs were rotated for 12 hours at a peripheral speed of 6 m/second. The temperature in the sand grinder was found to be 20° to 25° C. The content was filtered under pressure to obtain 40 g of a finely divided zinc salt dispersion. When the media were washed twice each with 70 g of water, 98% of the zinc salt could be recovered.

The finely divided zinc salt had, as shown in Table 5, a size distribution in which 91 wt % of the particles had a size below 0.1 micron.

EXAMPLE 11

14 g of a powder of zinc salt of 2-mercaptopyridine-N-oxide, 4.5 g of a water-soluble copolymer salt of the formula having a molecular weight of 320,000;

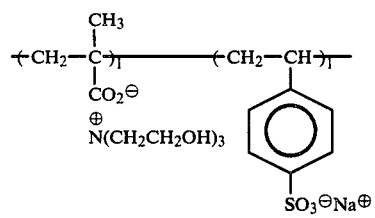

72 g of water, and 187 g of glass beads (media) having a size of 0.1 to 0.2 mm were mixed (media/dispersion ratio by volume=63/37) and placed in a 400 ml sand grinder (made by Igarashi Machine Manufacturing Co., Ltd.). In the grinder, discs were rotated for 12 hours at a peripheral speed of 6 m/second. The temperature in the sand grinder was found to be 20° to 25° C. The content was filtered under pressure to obtain 35 g of a finely divided zinc salt dispersion.

The finely divided zinc salt had, as shown in Table 5, a size distribution in which 77 wt % of the particles had a size below 0.1 micron.

EXAMPLE 12

14 g of a powder of zinc salt of 2-mercaptopyridine-N-oxide, 4.5 g of a water-soluble copolymer salt of the formula having a molecular weight of 100,000;

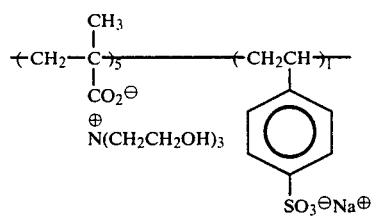

72 g of water, and 203 g of glass beads (media) having a size of 0.1 to 0.2 mm were mixed (media/dispersion ratio by volume=65/35) and placed in a 400 ml sand grinder (made by Igarashi Machine Manufacturing Co., Ltd.). In the grinder, discs were rotated for 3 hours at a peripheral speed of 6 m/second. The temperature in the sand grinder was found to be 20° to 25° C. The content was filtered under pressure to obtain 38 g of a finely divided zinc salt dispersion.

The finely divided zinc salt had, as shown in Table 5, a size distribution in which 50 wt % of the particles had a size below 0.1 micron.

TABLE 5

| Zinc Salt Dispersion | | Example 1 | | | Example 2 | | Example 3 |
|---|---|---|---|---|---|---|---|
| | | \multicolumn{6}{c}{Treating Time (hours.)} | |
| | | 3 | 5 | 12 | 6 | 12 | 3 |
| Size Distribution (wt %) | over 0.5 (μ) | 3% | 0 | 0 | 0 | 0 | 1 |
| | 0.5–0.2 | 12 | 1 | 2 | 2 | 3 | 12 |
| | 0.2–0.1 | 25 | 7 | 8 | 16 | 15 | 37 |
| | 0.1–0.05 | 46 | 70 | 35 | 62 | 37 | 36 |
| | below 0.05 | 14 | 22 | 55 | 20 | 45 | 14 |
| Average Size (μ) | | 0.09 | 0.07 | 0.05 | 0.07 | 0.06 | 0.10 |

EXAMPLE 13

23 g of a powder of zinc salt of 2-mercaptopyridine-N-oxide, 4.5 g of a water-soluble copolymer salt of the formula having a molecular weight of 260,000;

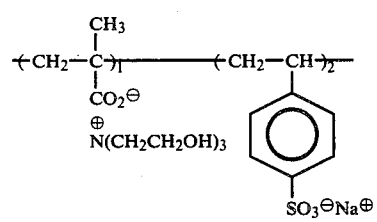

63 g of water, and 187 g of glass beads (media) having a size of 0.1 to 0.2 mm were mixed (media/dispersion ratio by volume=63/37) and placed in a 400 ml sand grinder (made by Igarashi Machine Manufacturing Co., Ltd.). In the grinder, discs were rotated for 8 hours at a peripheral speed of 6 m/second. The temperature in the sand grinder was found to be 20° to 25° C. The content was filtered under pressure to obtain 50 g of a finely divided zinc salt dispersion.

The finely divided zinc salt had, as shown in Table 6, a size distribution in which 100 wt % of the particles had a size below 0.1 micron.

EXAMPLE 14

23 g of a powder of zinc salt of 2-mercaptopyridine-N-oxide, 4.5 g of a water-soluble copolymer salt of the formula having a molecular weight of 380,000;

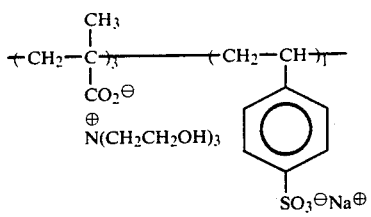

63 g of water, and 187 g of glass beads (media) having a size of 0.1 to 0.2 mm were mixed (media/dispersion ratio by volume=63/37) and placed in a 400 ml sand grinder (made by Igarashi Machine Manufacturing Co., Ltd.). In the grinder, discs were rotated for 8 hours at a peripheral speed of 6 m/second. The temperature in the sand grinder was found to be 20° to 25° C. The content was filtered under pressure to obtain 45 g of a finely divided zinc salt dispersion.

The finely divided zinc salt had, as shown in Table 6, a size distribution in which 100 wt % of the particles had a size below 0.1 micron.

EXAMPLE 15

23 g of a powder of zinc salt of 2-mercaptopyridine-N-oxide, 4.5 g of a water-soluble copolymer salt of the formula having a molecular weight of 350,000;

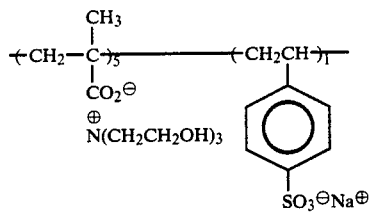

63 g of water, and 187 g of glass beads (media) having a size of 0.1 to 0.2 mm were mixed (media/dispersion ratio by volume=63/37) and placed in a 400 ml sand grinder (made by Igarashi Machine Manufacturing Co., Ltd.). In the grinder, discs were rotated for 8 hours at a peripheral speed of 6 m/second. The temperature in the sand grinder was found to be 20° to 25° C. The content was filtered under pressure to obtain 40 g of a finely divided zinc salt dispersion.

The finely divided zinc salt had, as shown in Table 6, a size distribution in which 100 wt % of the particles had a size below 0.1 micron.

TABLE 6

| Zinc Salt Dispersion | | Example 4 | Example 5 | Example 6 |
|---|---|---|---|---|
| Size | over 0.5 (μ) | 0 | 0 | 0 |
| Distri- | 0.5-0.2 | 0 | 0 | 0 |
| bution | 0.2-0.1 | 0 | 0 | 0 |
| (wt %) | 0.1-0.05 | 68 | 55 | 25 |
| | below 0.05 | 32 | 45 | 75 |
| Average Size (μ) | | 0.06 | 0.05 | 0.03 |

A zinc salt of 2-mercaptopyridine-N-oxide having an average size of 0.08 micron, was labeled with $^{35}S$. The labelled zinc salt was dispersed in 500 ml of an aqueous solution of 1% sodium polyoxyethylene(2) laurylsulfate. In the dispersion was placed 30 mg of a hair bundle, followed by immersing for 1 minute under agitation at 100 r.p.m. Subsequently, the hair bundle was rinsed twice each with running water for 15 seconds and air-dried, after which 10 mg of the hair was exactly weighed and placed in a 20 ml of vial. In the vial, it was dissolved in 1 ml of Soluen 350. To the solution was added 10 ml of a scientillator, followed by counting with a liquid scintillation counter to determine an amount of adsorbed and remaining zinc salt. The results are shown in Table 7.

TABLE 7

| Concentration of Zinc Salt Dispersion (%) | 0.5 | 1.0 | 1.5 | 2.0 |
|---|---|---|---|---|
| Product of Invention | 0.23 | 0.32 | 0.76 | 1.34 |

μg/10 mg of hair

EXAMPLE 17

| Dandruff Remover: | |
|---|---|
| Zinc salt (obtained in Example 7) | 2.0% |
| Propylene glycol | 5.0% |
| Ethanol | 10.0 |
| Perfume | very small amount |
| Water | balance |

The dandruff remover had a remarkable dandruff-removing effect and was stable over 3 months or more at room temperature.

EXAMPLE 18

An aqueous bactericidal composition of the following formulation using a zinc salt of 2-mercaptopyridine-N-oxide according to the invention was pepared.

| Zinc salt (average size 0.1μ) | 0.1 wt % |
|---|---|
| Spreader | 0.01 |
| Water | suitable amount |
| Total | 100.00 |

This aqueous bactericide was stable over 1 month or more and exhibited a good bactericidal effect when applied to trees.

EXAMPLE 19

| Dandruff Remover: | |
|---|---|
| Zinc salt (obtained in Example 11) | 2.0% |
| Propylene glycol | 5.0% |
| Ethanol | 30% |
| Perfume | very small amount |
| Water | balance |
| Total | 100% |

This dandruff remover had a remarkable dandruff-removing effect and was stable over 3 months or more at room temperature.

What is claimed is:

1. A finely divided zinc salt of 2-mercaptopyridine-N-oxide having a particle size distribution such that the particles which have a size less than 0.2 micron are present in amounts not less than 50 wt %.

2. An antibacterial composition, comprising: an effective amount of a finely divided zinc salt of 2-mercaptopyridine-N-oxide having a size distribution in which particles which have a size below 0.2 micron are present in amounts not less than 50 wt %, in a therapeutically acceptable carrier.

3. The zinc salt of claim 1, wherein the particles which have a size ranging from 0.5 to 1.0 micron are present in amounts not greater than 15 wt %, and the particles which have a size exceeding 1.0 micron are present in amounts not greater than 2 wt % of the particles, the average size of the particles being below 0.2 micron.

4. The zinc salt of claim 1 wherein the particles which have a size ranging from 0.5 to 1 micron are present in amounts not greater than 10 wt %, said particles being substantially free of particles exceeding 1.0 microns, with the average size of particles being below 0.15 microns.

5. The antibacterial composition of claim 2, wherein the particles which have a size ranging from 0.5 to 1.0 micron are present in amounts not greater than 15 wt %, and the particle which have a size exceeding 1.0 micron are present in amounts not greater than 2 wt % of the particles, the average size of the particles being below 0.2 micron.

6. The antibacterial composition of claim 2, wherein the particles which have a size ranging from 0.5 to 1 micron are present in amounts not greater than 10 wt %, said particles being substantially free of particles exceeding 1.0 microns, with the average size of particles being below 0.15 microns.

* * * * *